(12) United States Patent
Näfstadius (10) Patent No.: US 7,120,223 B2
(45) Date of Patent: Oct. 10, 2006

(54) BODY-SUPPORTING COUCH

(75) Inventor: Peder Näfstadius, Täby (SE)

(73) Assignee: Pencilbeam Technologies, Uppsala (SE)

( * ) Notice: Subject to any disclaimer, the term of this patent is extended or adjusted under 35 U.S.C. 154(b) by 56 days.

(21) Appl. No.: 10/253,695

(22) Filed: Sep. 25, 2002

(65) Prior Publication Data

US 2004/0057557 A1    Mar. 25, 2004

(51) Int. Cl.
*A61B 6/04*    (2006.01)

(52) U.S. Cl. .................. 378/20; 378/196; 378/209; 5/601

(58) Field of Classification Search .............. 378/65, 378/195, 196, 208, 209, 20; 5/81.1 R, 81.1 C, 5/81.1 HS, 601, 611, 86.1; 600/415, 425
See application file for complete search history.

(56) References Cited

U.S. PATENT DOCUMENTS

| | | | | |
|---|---|---|---|---|
| 3,466,439 A * | 9/1969 | Setala | ............. | 378/65 |
| 4,099,059 A * | 7/1978 | Distler | ............. | 378/17 |
| 4,131,802 A * | 12/1978 | Braden et al. | ............. | 378/20 |
| 4,575,064 A * | 3/1986 | Menor | ............. | 5/600 |
| 4,583,242 A * | 4/1986 | Vinegar et al. | ............. | 378/20 |
| 4,914,682 A | 4/1990 | Blumenthal | ............. | 378/20 |
| 5,013,018 A * | 5/1991 | Sicek et al. | ............. | 5/601 |
| 5,014,292 A | 5/1991 | Siczek et al. | ............. | 378/196 |
| 5,034,970 A * | 7/1991 | Yahata et al. | ............. | 378/20 |
| 5,151,931 A * | 9/1992 | Terashi et al. | ............. | 378/65 |
| 5,237,600 A | 8/1993 | Kamata | ............. | 378/177 |
| 5,475,884 A * | 12/1995 | Kirmse et al. | ............. | 5/601 |
| 5,525,905 A * | 6/1996 | Mohapatra et al. | ............. | 324/318 |
| 5,619,763 A * | 4/1997 | Randolph et al. | ............. | 5/601 |
| 5,724,400 A * | 3/1998 | Swerdloff et al. | ............. | 378/65 |
| 5,851,182 A * | 12/1998 | Sahadevan | ............. | 600/407 |
| 6,045,262 A * | 4/2000 | Igeta et al. | ............. | 378/209 |
| 6,322,251 B1 * | 11/2001 | Ballhaus et al. | ............. | 378/209 |
| 6,400,791 B1 * | 6/2002 | Schwarz | ............. | 378/17 |
| 6,416,219 B1 * | 7/2002 | Pflaum et al. | ............. | 378/209 |
| 6,640,364 B1 * | 11/2003 | Josephson et al. | ............. | 5/601 |
| 6,668,403 B1 * | 12/2003 | Seufert | ............. | 5/601 |
| 6,754,520 B1 * | 6/2004 | DeSilets et al. | ............. | 600/415 |
| 2002/0104163 A1* | 8/2002 | Reimann | ............. | 5/601 |

FOREIGN PATENT DOCUMENTS

| WO | 00/74779 A1 | 12/2000 |
|---|---|---|
| WO | WO 00/74779 A1 | 12/2000 |
| WO | 01/59478 A1 | 8/2001 |

* cited by examiner

*Primary Examiner*—Allen C. Ho
(74) *Attorney, Agent, or Firm*—Young & Thompson (57) ABSTRACT

A body-supporting couch and a radiation system incorporating such a couch are disclosed. The couch comprises a first and second couch unit, respectively. The first couch unit comprises a first table top support and a first elongated table top portion extending horizontally from the first support. The first table top portion is provided with a first docking element arranged in an end. Element for moving the first table top portion relative the first table top support along its longitudinal axis is arranged in the first couch unit. The second couch unit comprises a second table top support, which supports a second table top portion, provided with a second docking element in an end facing the first couch unit. Upon contact, the first docking element engages with the second docking element and the first table top portion connects with the second table top portion forming a stable continuous table top.

13 Claims, 8 Drawing Sheets

BODY-SUPPORTING COUCH

TECHNICAL FIELD OF THE INVENTION

The present invention generally relates to a body-supporting couch and in particular a stable two-part body-supporting couch, and a radiation therapy or diagnostic system incorporating such a couch.

BACKGROUND OF THE INVENTION

During the past decades there have been considerable developments within the field of radiation therapy and diagnostics. The performance of external beam radiation accelerators, brachytherapy and other specialized radiation equipment has improved rapidly. Developments taking place in the quality and adaptability of radiation beams have included new targets and filters, improved accelerators, increased flexibility in beam-shaping through new applicators, collimator and scanning systems and beam compensation techniques, and improved dosimetric and geometric treatment verification methods have been introduced.

Furthermore, a number of powerful 3-dimensional diagnostic techniques have been developed, ranging from computed tomography (CT), positron and single photon emission computed tomography (PET and SPECT) to ultrasound and magnetic resonance imaging, spectroscopy and spectroscopy imaging (MRI, MRS and MRSI). Equally important is the increased knowledge of the biological effect of fractionated uniform and non-uniform dose delivery to tumors and normal tissues and new assay techniques, including the determination of effective cell doubling times and individual tissue sensitives, allowing optimization of the dose delivery to tumors of complex shape and advanced stages.

Also new and improved designs of the constituent parts of a radiation therapy or diagnostic system, such as more stable and faster revolving gantries, have been developed. However, the body-supporting couches or tables of today, onto which a patient is positioned in a radiation therapy or diagnostic machine, are far from ideal, considering stability and user-friendliness issues.

Figure 1:
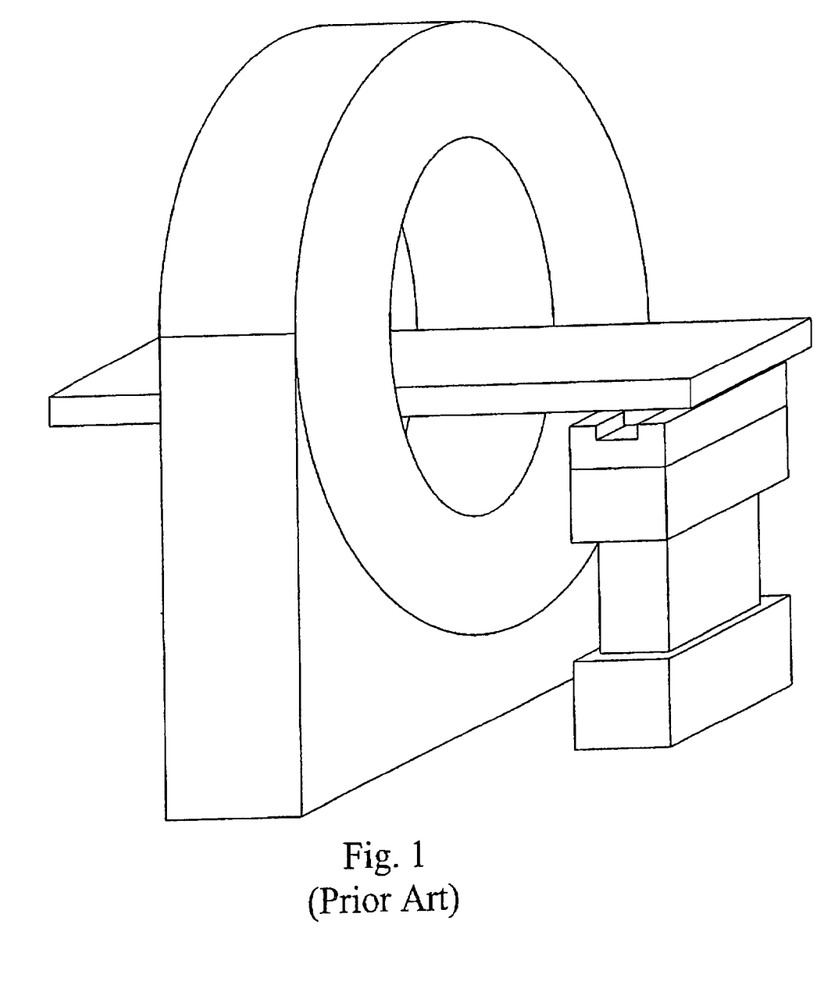
FIG. 1 is an illustration of a radiation therapy or diagnosing system incorporating a prior art body-supporting couch.

FIG. 1 is a schematic illustration of a typical prior art body-supporting couch in a radiation therapy or diagnostic system. The couch is supported at one end by a couch support, situated at one side of a gantry of a radiation therapy or diagnostic machine. During treatment or diagnostic work up, a patient is positioned on the couch where a radiation source of the gantry irradiates a target volume in the patient. For radiation therapy, high-energy beams irradiate the target volume, typically including all tumor tissues to be eradicated. In diagnosing, diagnostic beams, most often with a lower photon energy, are incident on the patient and a dedicated detector, arranged in the gantry, captures radiation passing through the patient and provides anatomical information, typically an image of the irradiated target volume.

However, it is rather complicated for the patient to get onto a couch designed according to FIG. 1. This is basically a twofold problem. Firstly, since the couch is arranged extending through the gantry, the accessible free space of the couch is limited to its ends. The patient therefore, more or less, has to crawl into correct couch position starting from one end. Secondly, the smallest possible height of the couch is limited by the height of the opening through the gantry. In most gantry designs today, this height is about 70 cm or sometimes even higher, which is far too large for a comfortable getting onto/off the couch. In addition, once on the couch, medical personnel typically have to reposition the patient slightly to align with a predetermined position, e.g. according to a dose or treatment plan. The large height of the couch makes this procedure cumbersome and hard, possibly leading to strain injuries of the personnel.

In order to increase accessibility of the couch, a swingable patient couch or table may be used. In U.S. Pat. No. 5,014,292 an X-ray examination apparatus is described. The apparatus comprises a base assembly, including a pivotally and vertically displaceable frame, a first actuating means for pivotal movement of the frame about a horizontal axis and a second actuating means for vertical movement of the frame, two parallel rail systems supported by the frame and having two carriages mounted respectively thereon. One of the carriages supports a C- or U-shaped carriage for supporting an X-ray source and image receptor and the other carriage has an overhanging support secured thereto. This support in turn includes a dual action mechanism for supporting a patient table in an arrangement providing its vertical movement relative the frame and its pivoting movement about an axis parallel to its longitudinal axis.

The couch design described above may be rotated away from the gantry to facilitate getting onto/off the couch. However, since only one couch support, arranged at one end of the table top, is used (as for the couch in FIG. 1) once the patient is positioned on the couch it bends slightly due to the patient's weight. This bending depends on the actual position of the patient and is therefore complex to calculate in advance and compensate for. In radiation diagnoses and especially in radiation therapy, the actual position of the patient has to be accurately known to safely deliver the radiation dose correctly to the target volume. Any such significant bending of the couch makes a correct dose delivery very hard and in some applications practically impossible.

In U.S. Pat. No. 5,237,600 a height-adjustable patient support couch for use with an X-ray camera apparatus is disclosed. The couch includes a hydraulic multi-stage piston-cylinder, of which a top piston is driven in a vertical direction, a drive unit for driving the pistons in an axial direction and a multi-stage supporting device for supporting an overhanging load exerted by a patient on a couch or table top.

The patient support couch in U.S. Pat. No. 5,237,600 suffers from similar stability problem as U.S. Pat. No. 5,014,292 due to only one couch support, which was discussed above. In addition, if used with a radiation therapy or diagnostic machine with a circular gantry, the free accessible space of the couch is limited to its ends. This makes getting onto/off the couch very troublesome for the patient.

SUMMARY OF THE INVENTION

The present invention overcomes these and other drawbacks of the prior art arrangements.

It is a general object of the invention to provide a stable body-supporting couch.

It is also an object of the invention to provide a body-supporting couch well adapted for use in a radiation therapy or diagnostic system.

Yet another object of the invention is to provide a user-friendly body-supporting couch allowing an easy getting onto/off the couch and comfortable patient positioning on the couch.

A further object of the invention is to provide a radiation therapy or diagnostic system incorporating a radiation machine and a body-supporting couch.

These and other objects are met by the invention as defined by the accompanying patent claims.

Briefly, the general concept of the present invention is to provide a body-supporting or stereotactic couch essentially comprising of two units, a first couch unit and a second couch unit, respectively. The first couch unit in turn comprises a first table top support and a first elongated table top portion extending substantially horizontally from the first table top support. This first table top portion is provided with a first docking means arranged in one of its ends or short sides. Furthermore, means for moving the first table top portion relative the first table top support along its longitudinal axis is arranged in the first couch unit. Similarly, the second couch unit comprises a second table top support, which supports a second table top portion. This second table top portion is provided with a second docking means in an end facing the first couch unit. Due to the longitudinal movable means, the first table top portion can be moved towards the second couch unit. Upon contact, the first docking means engages and docks to the second docking means, possibly also reversibly locks thereto. The first table top portion then connects with the second table top portion forming a very stable continuous table top.

The first couch unit is preferably also provided with height-adjusting means for raising/lowering the first table top portion and a patient positioned thereon. In addition, means for lateral movement, perpendicular to the longitudinal axis of the first table top portion, and rotating means may also be arranged for lateral movement and turning or rotation of the first table top portion, respectively.

The second couch unit preferably comprises means for moving the second table top portion along an axis parallel with the longitudinal axis of the first table top portion when the first and second docking means are engaged, i.e. the first table top portion is connected to the second table top portion. In addition, biasing means may be arranged in the second couch unit for providing a biasing force on the second table top portion towards the first couch unit. An arc-portion, the center of curvature of which coincidences with the rotation axis of the first couch unit, may be provided on the second table top support. The second couch unit then preferably comprises means for moving the second table top portion along the arc. Also means for lateral movement and possibly height-adjusting means may also be provided in the second couch unit, similar to the first couch unit.

The couch may be used for radiation applications in a radiation therapy or diagnostic system together with a radiation machine. Such a machine typically includes a gantry support, with a cylindrical opening therethrough, rotatably supporting a ring-shaped gantry. The gantry is arranged on the gantry support so that its rotation axis coincidences with the axis of the opening. A radiation head with a radiation source is circumferentially arranged on the gantry. The first couch unit is then arranged on one side of the gantry with its rotation axis passing through the radiation source when the source is in its uppermost position. The second couch unit is arranged on the other opposite side of the gantry, possibly on the gantry support.

For positioning of a patient on the couch, the first table top portion is first moved away from the gantry and lowered, which allows easy getting onto the couch. A laser system may be used for aligning the patient according to e.g. a dose or treatment plane in this low position. The height of the first table top portion and the patient in this position facilitate any alignment and repositioning of the patient by the medical personnel, reducing the risk for strain injuries. The first table top portion with the patient thereon is then raised until the rotation axis of the gantry passes through the target volume and is moved towards the second couch unit. The first couch unit then connects to the second couch unit through the docking means, forming a continuous table top and the radiation therapy treatment or diagnosing can be started.

The invention offers the following advantages:
Very stable couch design;
Allowing an easy getting onto/off the couch;
Comfortable positioning of a patient on the couch with reduced risk for strain injuries for medical personnel;
Adapted for allowing delivery of radiation doses in planes other than the orthogonal plane; and
Adapted for allowing irradiation of a patient's head.

Other advantages offered by the present invention will be appreciated upon reading of the below description of the embodiments of the invention.

BRIEF DESCRIPTION OF THE DRAWINGS

The invention, together with further objects and advantages thereof, will be best understood by reference to the following description taken together with the accompanying drawings, in which.

DETAILED DESCRIPTION OF EMBODIMENTS OF THE INVENTION

The invention refers to a body-supporting couch or table onto which a patient is positioned. The couch may be used in a radiation system together with a radiation machine delivering a dose package or radiation beam, such as a beam of gamma photons, electrons, neutrons, protons or heavier ions, atoms or molecules, to a target volume in the patient. According to the present, radiation systems or machines relate to diagnostic and radiation therapy systems and machines, respectively.

A diagnostic system incorporates a diagnostic or imaging machine, used to obtain anatomical information of a patient positioned on a couch, including localization of tumors and adjacent tissues and organs, based on different imaging techniques. Such imaging techniques may be e.g. computed tomography (CT), including conventional CT and cone-beam CT imaging, radiation therapy CT (RCT) and other diagnostic X-ray techniques, positron emission computed tomography (PET), single photon emission computed tomography (SPECT), combined PET and CT (PET/CT), ultrasound, magnetic resonance (MR) techniques, e.g. magnetic resonance imaging (MRI), magnetic resonance spectroscopy (MRS) and magnetic resonance spectroscopy imaging (MRSI) and other imaging techniques.

A radiation therapy system includes a radiation therapy machine that applies a dose package or radiation beam to a patient positioned on a couch, usually based on anatomical information obtained from a diagnostic system. The radiation therapy machine may be employed for curative radiation therapy, i.e. to eradicate a tumor, or palliative radiation therapy, where the aim is generally to improve quality of life of the patient by maintaining local tumor control, relieve a symptom or prevent or delay an impending symptom, and not primarily to eradicate the tumor. Yet another application of a radiation therapy machine may be in radiosurgery using a high-energy radiation source.

Although a body-supporting couch according to the present invention is well-adapted for use in a radiation system, where the stability demands are very heavy, the couch may be used in other applications, e.g. as a surgery couch or table, in particular for robotic surgery applications, but also in non-medical applications.

Figure 2A:
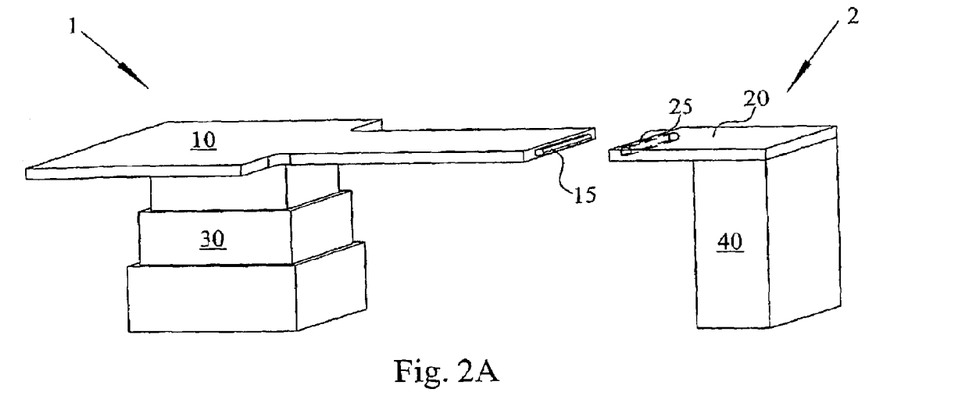
FIG. 2A is an illustration of an embodiment of a body-supporting couch according to the present invention with the table top portions separated.
Figure 2B:
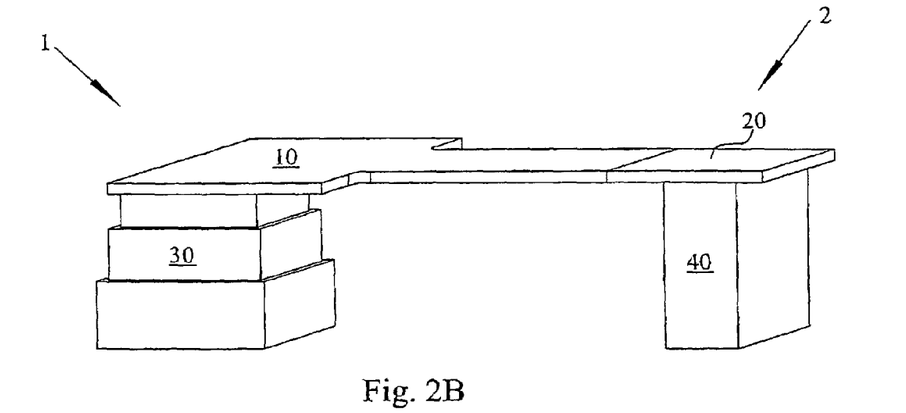
FIG. 2B is an illustration of the couch in FIG. 2A with the table top portions connected, ready for radiation delivery.

A first embodiment of a body-supporting couch according to the present invention is schematically illustrated in FIGS. 2A and 2B. The couch comprises a first couch unit 1 and a second couch unit 2, respectively. The first couch unit 1 in turn comprises a first table top portion 10 arranged on and extending substantially horizontally from a first table top support 30. This first table top portion 10 is movable relative the first table top support 30 along its longitudinal axis. Therefore, due to movable means (not illustrated) in the first couch unit 1, the first table top portion 10 can be moved away from, FIG. 2A, or towards, FIG. 2B, the second couch unit 2. This second couch unit 2 in turn includes a substantially horizontal second table top portion 20 supported by a second table top support 40.

In the end or short side, or in the vicinity thereof, of the first table top portion 10 facing the second couch unit 2, a first docking means 15 is provided. A corresponding second docking means 25 is likewise arranged in the end of the second table top portion 20 facing the first couch unit 1. When the first table top portion 10 is moved towards the second couch unit 2, it gradually touches or connects with the second table top portion 20 through the docking means 15, 25. Upon contact, the first docking means 15 engages or docks with the second docking means 25. In other words, the second docking means 25 guides the first docking means 15, and consequently the first table top portion 10, into correct position relative the second table top portion 20.

In a first embodiment, the first docking means 15 is a protrusion protruding from an end of the first table top portion 10, whereas the second docking means 25 is a corresponding dedicated slot arranged in the second table top portion 20, as in FIG. 2A. However, the second docking means 25 may instead include a protrusion with the first docking means 15 as a dedicated slot. A protrusion with a corresponding slot, is merely an example of complementary means that may be used for guiding the first table top portion 10 into correct position relative the second table top portion 20. Other possible embodiments may include magnets etc. In addition, the first 15 and/or second 25 docking means may include locking means for reversible locking the first table top portion 10 to the second table top portion 20 in the correct position. By 'reversible locking' means that the first table top portion 10 may be locked to the second table top portion 20, but also be 'unlocked' therefrom, i.e. the locking is unlocked so that first table top portion 10 can be moved again away from the second table top portion 20. Here magnets or other reversible locking means may be used. Once the first 10 and second 20 table top portions connects and possibly locks to each other, a continuous table top is formed, as in FIG. 2B.

Figure 3A:
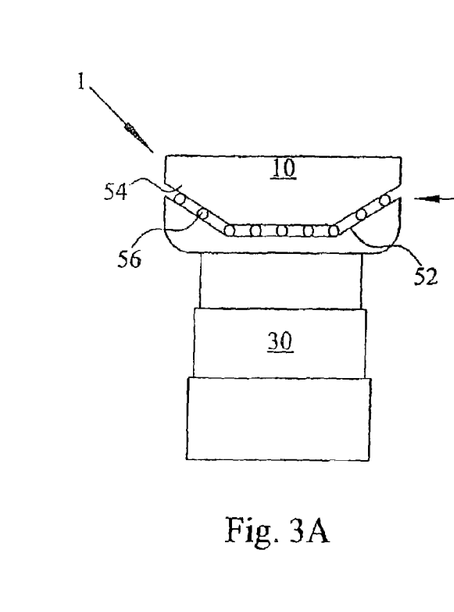
FIGS. 3A and 3B illustrate two different embodiments of a first couch unit according to the present invention.

FIG. 3A is an embodiment of the first couch unit 1 illustrating a movable means 50 for moving the first table top portion 10 relative the first table top support 30. In this embodiment the movable means 50 comprises a protrusion 54 connected to the first table top portion 10. This protrusion 54 has a general trapezoid-shaped cross-section. A dedicated associated slot 52 is arranged on the first table top support 30, along which the protrusion 54 and thus the first table top portion 10 can be moved. In addition, a layer of balls 56 may preferably be provided in the slot 52 to facilitate the movement. As a skilled person understands, protrusion and associated slots with cross-sections other than trapezoid-shapes may be used according to the present invention. Also, more than one protrusion-slot system may be used for the longitudinal movement of the first table top.

Figure 3B:
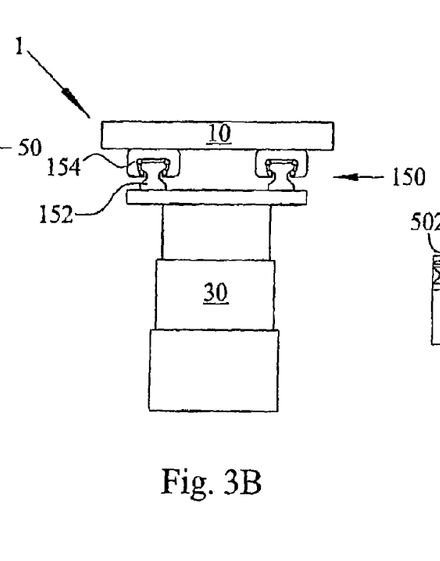

FIG. 3B illustrates another embodiment of longitudinal movable means 150 of the first couch unit 1. This movable means 150 comprises a system of at least one rail 152 and dedicated carriage 154. The rail 152 is arranged on the first table top support 30, whereas the carriages 154 are connected to die first table top portion 10. As the carriages 152 move along the rail 154, the first table top 10 is moved relative the first table top support 30. A typical rail-carriage system applicable with the present invention is Linear Motion (LM) Guides from THK Co., Ltd., Japan.

Although, the movable means of FIGS. 3A and 3B are provided in the interface between the first table top portion and the first table top support, the movable means may instead be arranged in the first table top support. In such a case, an upper first table top support and the first table top portion moves relative a lower first table top support. The first table top portion may be moved manually, i.e. a person pushes the table back or forth. However, driving means may be provided in connection to or in the first couch unit for driving the movable means. Then, the first table top portion may automatically may be moved relative the first table top support.

Figure 2C:
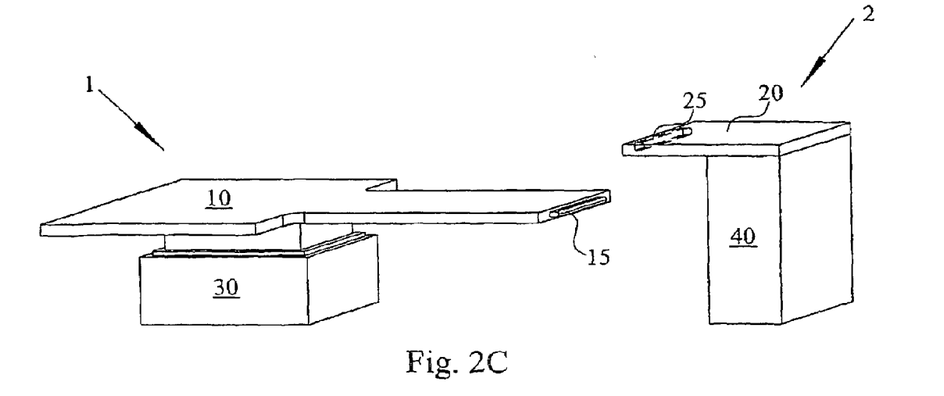
FIG. 2C is an illustration of the couch in FIGS. 2A and 2B with a height-adjustable functioning.

In a preferred embodiment of the body-supporting couch, the first table top portion is also movable along a vertical axis, i.e. the height of the first table top portion is adjustable. FIG. 2C illustrates a body-supporting couch with a height-adjustable functioning. In this embodiment, the first couch unit 1 comprises height-adjusting means (not illustrated), preferably in the first table top support 30 or in the interface between the first table top support 30 and the first table top portion 10.

Figure 4A:
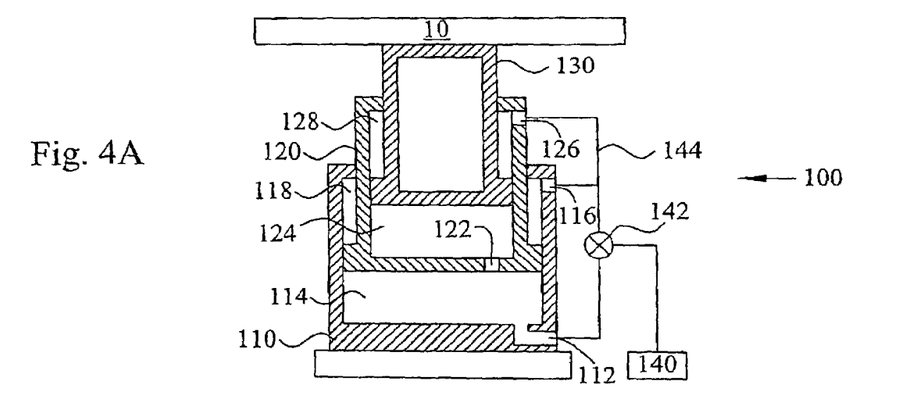
FIGS. 4A to 4C are embodiments of height-adjusting means usable in a first couch unit according to the present invention.
Figure 4B:
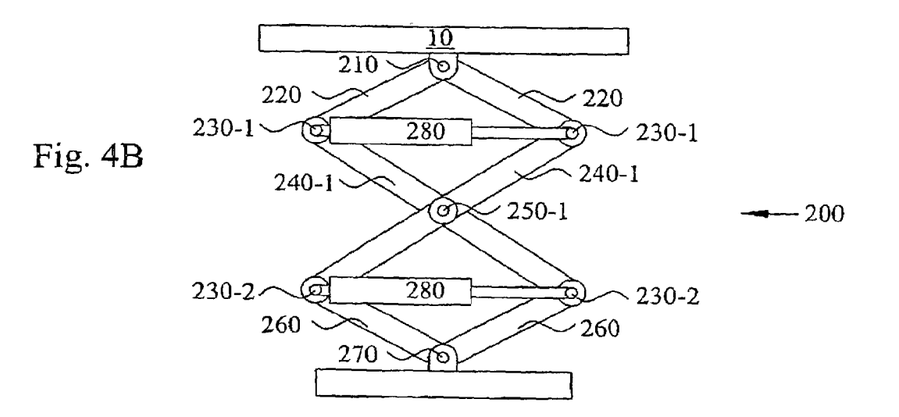
Figure 4C:
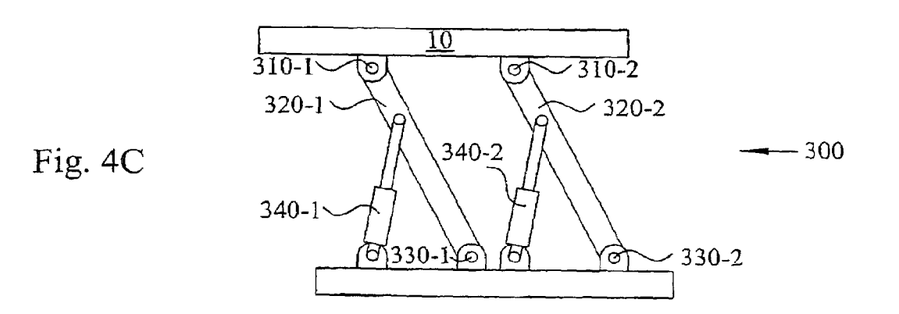

FIGS. 4A to 4C illustrate embodiments of height-adjusting means that can be used in the first couch unit.

Starting with FIG. 4A, a cross section of a height-adjusting means 100 in form of a hydraulic multi-stage piston-cylinder system is illustrated. The system comprises a base cylinder 110, a first piston 120 formed as a block with a second cylinder, which slides in the base cylinder 110. In the cylinder of the first piston 120, a top piston 130, connected to the first table top portion 10, is slidably arranged.

The base cylinder 110 is provided with a lower oil port 112 in the bottom thereof and an upper oil port 116 in its upper portion. The first piston 120 has likewise a lower 122 and an upper 126 oil port, respectively. The lower oil port 122 connects a chamber 124, formed by the arrangement with the top piston 130 in the cylinder of the first piston 120, to a similar chamber 114, formed by the first piston 120 arranged in the base cylinder 110. The oil ports 112, 116 of the base cylinder 110 and the upper oil port 126 of the first piston 130 are connected through oil pipes 144 to a switch valve 142, in turn connected to an oil compressing means 140, such as an oil pump or a plunger pump.

To raise the first table top portion 10, high pressure oil flows through the lower oil port 112 into the chamber 114 and pushes the first piston upwards. At the same time, oil flows from the lower chamber 114 into the upper chamber 124 through the oil port 122 therebetween. Therefore, also the top piston 130 and the first table top portion 10 is pushed upwards. Oil in chambers 118 and 128 flows out through respective ports 116 and 126. The oil ports are preferably designed so that the first piston 120 and the top piston 130 moves with the same speed when the high pressure oil flows in through the lower oil port 112.

In order to lower the first table top portion 10, the valve 142 is switched so that the oil compressing means 140 provides high pressure oil to the upper oil ports 116, 126. At the same time oil flows from the upper chamber 124 into the lower chamber 114, through the oil port 122 therebetween, and then out through the lower oil port 112 as the pistons 120, 130 and the first table top portion 10 descend.

The height-adjusting means 100 is provided with sealing rings for maintaining the high oil pressures without any leakage.

Although, the height-adjusting means in FIG. 4A is illustrated with a base cylinder, a first piston and a top piston, other arrangements are possible. For example, the first piston may be omitted so that the system only comprises the base cylinder and the top piston. The maximal height-increase is then somewhat smaller than twice the height of the base cylinder. By instead arranging one or several additional pistons (one in FIG. 4A) between the base cylinder and the top piston, the maximal height-increase may be several limes the height of the base cylinder. In such a case, a base cylinder with a rather small height may be employed yet achieving an adequate height of the first table top portion in the uppermost position. In other words, using several intermediate pistons makes it possible to achieve a small lowest height and a large highest height of the first table top portion, which may be advantageous in some applications.

FIG. 4B illustrates another embodiment of a height-adjusting means 200 of the first couch unit. This adjusting means 200 comprises a series of interconnected links and joints. To the first table top portion 10 an upper pin joint 210 is connected. Two upper links 220, 220 are rotatably connected to the upper pin joint 210. Intermediate links 240-1, 240-1 are rotatably arranged in a first end to the upper links 220, 220 through joints 230-1, 230-1. The intermediate links 240-1, 240-1 are in turn interconnected with a rotatable intermediate joint 250-1, preferably situated in the middle of the intermediate links 240-1, 240-1. In the other opposite end of the intermediate links 240-1, 240-1 they are connected to lower links 260, 260 through joints 230-2, 230-2. These lower links 260, 260 are in turn interconnected through a lower pin joint 270. The height-adjusting means 200 also comprises driving means 280 for raising or lowering the first table top portion 10. The driving means 280 may for example be hydraulic piston-cylinder units arranged between the joints 230-1, 230-1 and 230-2, 230-2.

In order to raise the first table top portion 10, the pistons of the driving means 280 are pushed into the associated cylinders. This movement pulls the joints 230-1, 230-1 and 230-2, 230-2 together so that the distance therebetween is reduced. At the same time, the first table top portion 10 is, through the interconnected system of links and joints, pushed upwards and raised. The opposite procedure is performed when the table top 10 descends.

In some applications with low height demands, the intermediate links 240-1, 240-1 and joint 250-1 may be omitted so that the upper joints 220, 220 are connected directly to the lower joints 260, 260. In order to increase the maximal height of the first table top, a series of several intermediate links and joints may be used, though the stability of the first couch unit may be somewhat reduced if too many intermediate links and joints are employed.

Yet another embodiment of a height-adjusting means 300 in the first couch unit is illustrated in FIG. 4C. This adjusting means 300 includes a number of, preferably two or more, pin joints 310-1, 310-2 arranged on the first table top portion 10. To these pin joints 310-1, 310-2 links 320-1, 320-2 are rotatably connected in one of their ends. In the other opposite end the links 320-1, 320-2 are rotatably connected to associated lower pin joints 330-1, 330-2.

Driving means 340-1, 340-2, e.g. hydraulic piston-cylinder units, are connected to the links for providing a pushing or a pulling force for raising or lowering the first table top portion 10, respectively. In its lowest position the first table top portion 10 is displaced laterally relative the base of the first table top support. At the same time as the first table top portion 10 is raised, it is also moved laterally towards the first table top support. Thus, as the first table top portion 10 is raised or lowered, it is moved along an arc-shaped path. Therefore this embodiment is primarily applicable where there is enough free space available for the first table top portion 10 to perform this arc-shaped raise/lowering.

Other height-adjusting means may instead be used, such as screw-nut assemblies. However, the adjusting means should preferable be stable enough to support the first table top portion with a patient thereon. In addition, the total space required for the adjusting means should not be too large, preferably not protrude past the sides of the first table top portion. The minimal height of first table top portion, achieved by the adjusting means should be low enough to make it easy for a patient to easily lay down on the first table top portion. In addition, any repositioning or movement of the patient at this height should be comfortably performable by medical personnel without any or only a low risk for strain injuries. The height-adjusting means may be arranged in the interface between the first table top portion and the first table top support or may constitute a part of the first table top support.

Returning to FIGS. 2A to 2C, thus according to the present invention, when a patient is to be positioned on the couch for e.g. radiation therapy or diagnosing, the first table top portion 10 is first moved away from the second couch unit 2 and lowered, as is illustrated in FIG. 2C. At this low height the patient may easily get onto the first table top portion 10 and any repositioning may be comfortably performed. Once correctly positioned, the first table top 10 with the patient is raised until aligned with the height of the second table top portion 20, which is shown in FIG. 2A. Thereafter the first table top portion 10 is moved along its longitudinal axis towards the second couch unit 2 until the first docking means 15 engages and possible locks to the second docking means 25, illustrated in FIG. 2B. Now the first 10 and second 15 table top portions forms a continuous and very stable table top, supported in either end by the first 30 and second 40 table top support, respectively. When the patient is to get off the couch, the opposite procedure is performed, i.e. the first table top portion 10 is moved away from the second couch unit 2 (FIG. 2A) and is lowered (FIG. 2B), allowing easy getting off the first table top portion 10.

As the patient is lying primarily on the first table top portion 10 it is preferably made of a strong and inflexible or stiff material in order to reduce any bending thereof due to the patient's weight when the first table top 10 is not yet connected to the second table top 20 (FIGS. 2A and 2C). Thus, the general function of the docking means 15, 25 is to guide the first table top 10 so that its height aligns with the height of the second table top support 20 (FIG. 2B). In addition, the material of the section of the first table top portion, through which any radiation is passing, preferably has low radiation absorption. Typical material could be different carbon fiber materials, e.g. a honeycomb carbon fiber panel. For a diagnostic system this means that the first table top portion preferably should absorb as little of any diagnostic radiation as possible passing through the patient and the first table top portion before being collected by a detector. In a radiation therapy system, sometimes the dose package is delivered from below the patient. Then adequate radiation dose should be allowed to pass through the first table top portion with as little absorption as possible before hitting the target volume in the patient.

The first couch unit may preferably also comprise lateral movable means for moving the first table top portion relative the first table top support along a substantially horizontal axis perpendicular to the longitudinal axis of the first table top portion. Such an horizontal lateral movement may be performed by movable means similar to those applicable for the horizontal longitudinal movement of the first table top portion, i.e. means similar to those discussed in connection to FIGS. 3A and 3B. This lateral movable means may be used for adjustment of the position of a patient on the first table top portion so that the radiation beam passes through the target volume in the patient.

Figure 6:
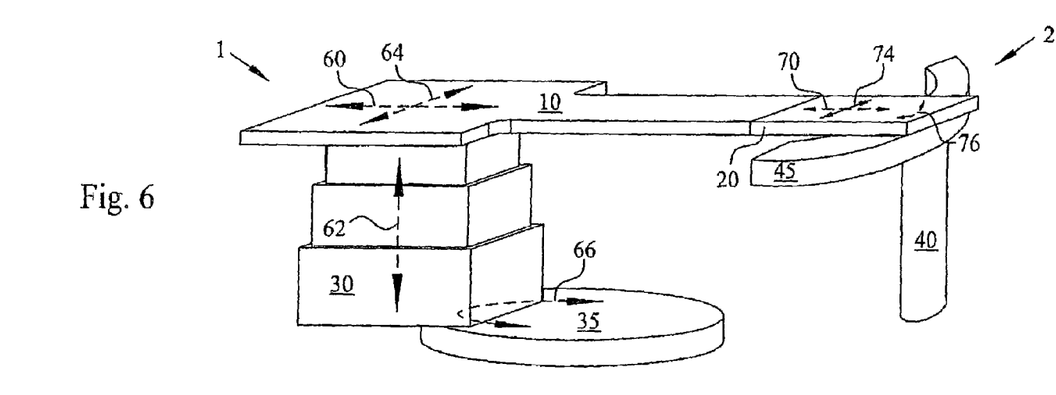
FIG. 6 is a schematic illustration of relative movements of relevant parts in a preferred embodiment of a body-supporting couch according to the present invention.

Turning to FIG. 6, the preferred relative movements of the first couch unit 1 are visualized. Firstly, the first table top portion 10 is movable relative the first table top support 30 along its longitudinal axis 60. This movement is used for pushing the first table top portion 10 and a patient lying thereon in through a gantry of a radiation machine so that the radiation beam passes through the target volume in the patient. In addition, the first table top portion 10 connects to the second table top portion 20 of the second couch unit 2, forming a stable continuous table top. Secondly, the height of the first table top portion 10 can be adjusted, i.e. the first table top portion 10 may be raised/lowered along a vertical axis 62. This height-adjustment makes an easy getting onto/off the couch possible besides reducing the risk for strain injuries during a repositioning of the patient on the couch. A lateral movement 64 of the first table top portion 10 is also preferred.

In radiation applications, it is also preferred to turn or rotate 66 the first couch unit 1. Such a turning 66 makes it possible to radiate the target volume in planes other than the orthogonal plane, which may be important in some radiation treatments. As can be seen in FIG. 6, the turning or rotation 66 of the first couch unit 1 is provided by e.g. a rotatable disk or similar means 35. As is more clearly illustrated in FIG. 8, the rotatable means 35 may include a circular rail arranged on the floor. Along the rail carriages, connected to a disk, may be moved, leading to a rotation of the disk. The first table top support 30 is then arranged on the disk, or the disk constitutes a (lower) part of the first table top support 30. A typical circular rail-carriage system is the R Guide HCR from THK Co., Ltd., Japan.

Figure 5:
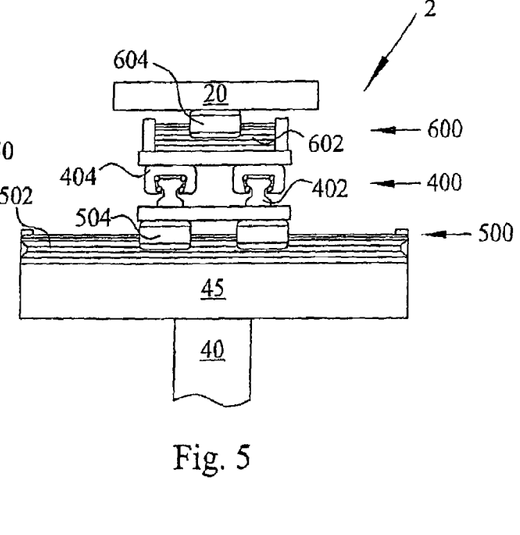
FIG. 5 illustrates an embodiment of a second couch unit according to the present invention.

The second couch unit 2 also preferably comprises means for movement of the second table top portion 20 relative the second table top support 40. In FIG. 5, an upper part of the second couch unit 2 with the corresponding means for accomplish these movements are illustrated.

Movable means 400 is used for moving the second table top portion 20 along an axis that is parallel to the longitudinal axis of the first table top portion when the first docking means faces (or is engaged with) the second docking means. This movable means 400 (together with the corresponding means of the first couch unit) makes it possible to move the first and second table top portions back and forth along the longitudinal axis when they are connected through the docking means. The means 400 preferably comprise a rail-carriage system. Then the second table top portion 20 may be moved relative the second table top support 40 by moving carriages 404 along rails 402. Alternatively, other movable means, such as protrusion with dedicated slot may be used.

In addition, the second couch unit 2 preferably comprises biasing means (not illustrated), such as a spring, for providing a biasing force pushing the second table top portion 20 towards the first couch unit by means of the movable means 400. This results in that when the second table top portion 20 is not connected to the first table top portion, it is displaced towards the first couch unit extending from the second table top support 40 by the biasing force (see FIGS. 2A and 2C). However, when the first and second docking means engage and the first table top portion connects to the second table top portion 20, the first table top portion pushes the second table top portion 20 slightly against the direction of the biasing force (se FIG. 2B). In this position, due to the biasing means, the first and second docking means fits tightly and the first and second table top portions form a continuous table top.

The second couch unit 2 may also comprise an arc portion 45, e.g. in the interface between the second table top portion 20 and the second table top support 40 or may be arranged in the second table top support 40. The center of curvature of the arc portion 45 is preferably situated at the rotation axis of the first couch unit, i.e. the rotation axis of the rotatable disk of the first couch unit. On the arc portion 45 means 500 for moving the second table top portion 20 along the arc 45 is arranged. Arc-shaped rails 502 with carriages 504 movable thereon may be used.

As for the first couch unit, the second couch unit 2 may also comprise lateral movable means 600 for moving the second table top portion 20 along a lateral axis, performing a movement substantially perpendicular to the longitudinal movement of means 400. Once again rails 602 with associated carriages 604 may be used, but also a protrusion-slot system is possible.

The corresponding preferred movements of the second couch unit 2 are shown in FIG. 6. Longitudinal movable means provides movement along the longitudinal axis 70 with a biasing force pushing the second table top portion 20 towards the first couch unit 1. Also lateral movement 74 perpendicular to the longitudinal axis 70 is possible. Finally, the arc portion 45 with associated movable means provides a rotating movement 76 of the second table top portion 20, the rotation center of which coincidences with the corresponding rotation axis of the first couch unit 1.

To sum up, when the first 10 and second 20 table top portions are connected their longitudinal 60 and 70, lateral 64 and 74 and rotating 66 and 76 movements coincidence so that the first 10 and second 20 table top portions move as one single unit. In addition, although not illustrated in FIG. 6, the second couch unit 2 may comprise height-adjusting means for raising/lowering the second table top portion 20. Then also the height of the continuous table top formed by the first 10 and second 20 table top portions may be adjusted up and down.

Each of, or some of, the longitudinal movable means, lateral movable means, rotating means, arc movable means and height-adjusting means of the first and second couch unit discussed above, may be connected to driving means for automatic movement of the first and second table top portion, respectively. Such driving means may be arranged in or on the respective couch unit and/or in connection thereto. The driving means may be manually driven by the medical personnel and/or could be connected to for example a computer for automatic adjustment/movement according to a predetermined plan.

Figure 7:
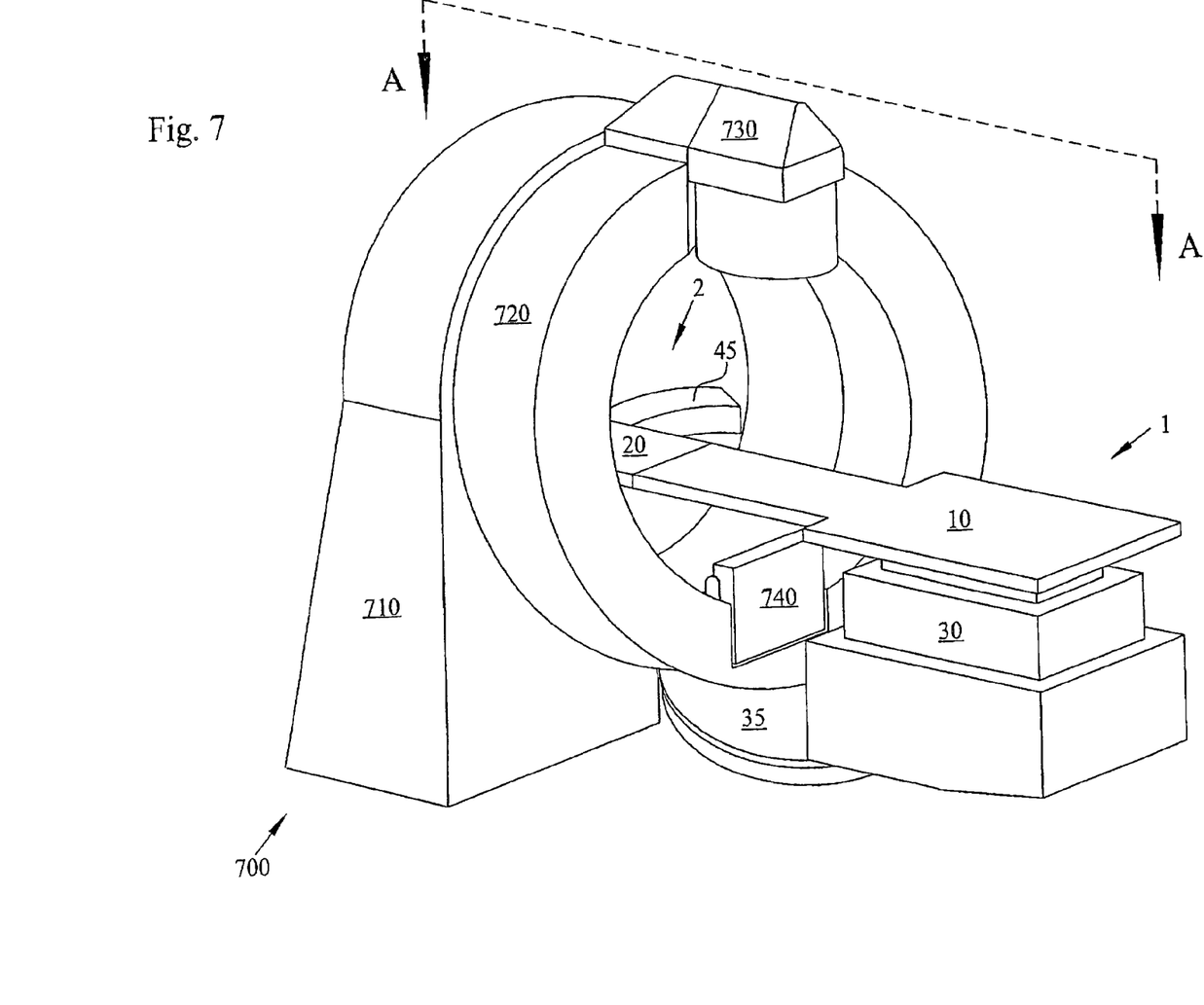
FIG. 7 is a perspective view of a radiation system incorporating a body-supporting couch according to the present invention.

FIG. 7 is a perspective view of a radiation system with a radiation machine 700 and a body-supporting couch according to the present invention. A sectional view of the system illustrated in FIG. 7 taken along the line A—A is shown in FIG. 8.

Starting with the radiation machine 700, a gantry support 710 with a cylindrical hole or opening therethrough rotatably supports a circular gantry 720. The rotation axis 760 of the gantry 720 coincidences with the axis of the opening through the gantry support 710. The mechanical operation and support of the rotatable gantry 720 is easily provided with e.g. conventional gear solutions and bearings. By also introducing sliding contacts between the gantry 720 and the gantry support 710, preferably in connection with the mechanical bearing, a true continuous rotational motion may be achieved. A radiation head 730 including a radiation source 735 is mechanically circumferentially arranged on the gantry 720. The design of the radiation head 730 is preferably such that as small part as possible of die radiation head 730 extends past the gantry 720 along the rotation axis 760. With such an arrangement, a very stable gantry design is accomplished, which in turn makes a fast rotation of the gantry 720 and the radiation head 730 around the rotation axis 760 possible without any major movement artifacts. A fast rotating gantry is important both for diagnostic and therapy applications. In diagnosing, an image of the patient is constructed as the gantry rotates around the patient and a detector captures radiation. If the rotation speed is too low the patient probably will move slightly during the recordings leading to a blur and inaccurate image. In addition to the stable design, this radiation machine arrangement takes only up a relative small deal of space compared to other fast rotating radiation machines.

Figure 8:
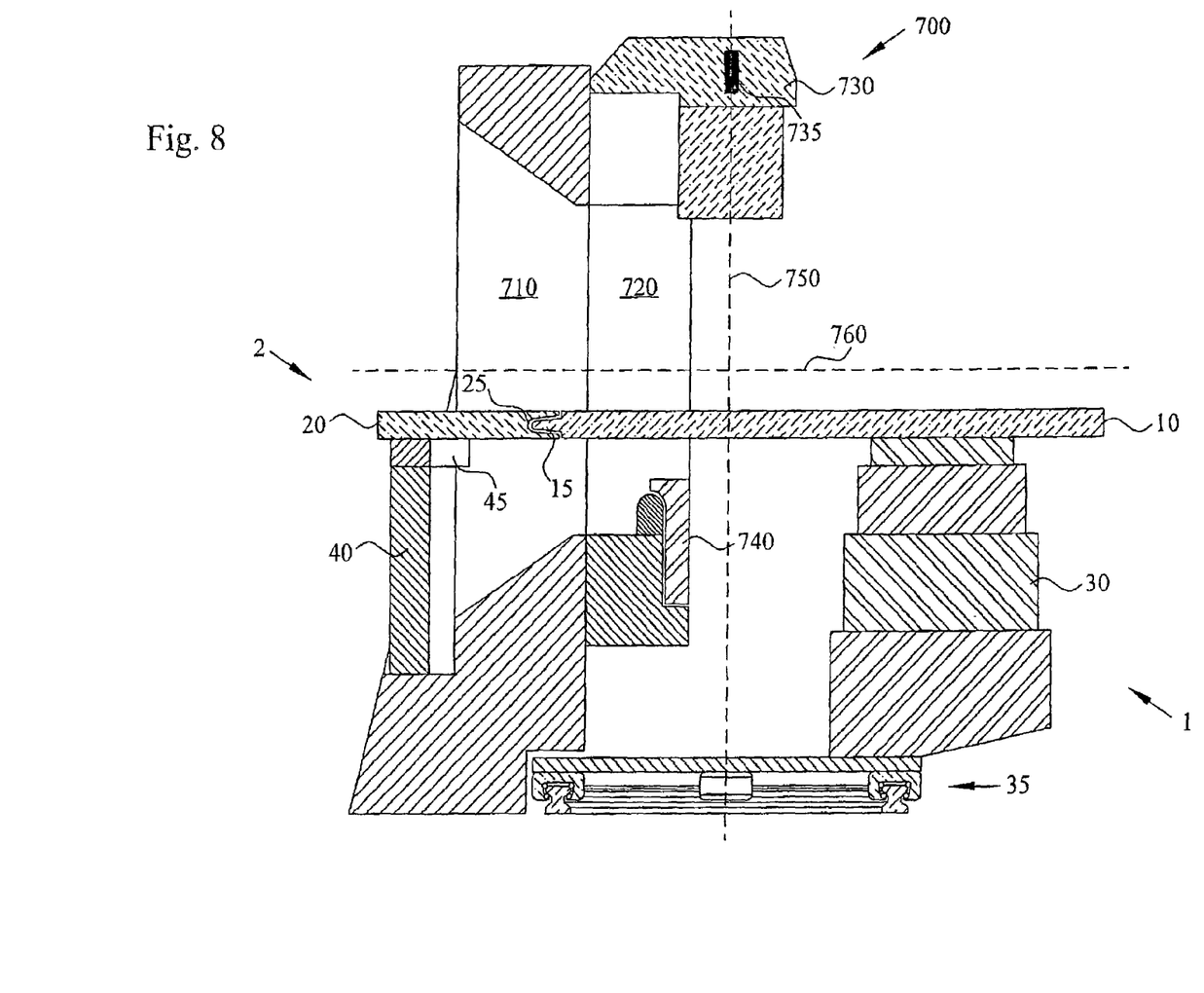
FIG. 8 is a sectional view of the system illustrated in FIG. 7 taken along the line A—A.

The body-supporting couch according to the present invention may also be used in radiation systems with other designs of the radiation machine than illustrated in FIGS. 7 and 8. For example, the couch may be used together with a radiation machine as illustrated in FIG. 1 or the stable radiation machine disclosed in the international patent application WO 00174779 A1 by Näfstadius.

An optional detector 740 may also be provided on the gantry 720 capturing radiation from the radiation source 735 passing through the patient. Preferably, the detector 740 is turnably or pivotally attached to the gantry 720. With such an attachment, the detector 740 is folded up when not used (as in FIGS. 7 and 8) and is turned up during use. The sliding contacts between the gantry 720 and gantry support 710 provides continuous connection between the detector 740 and image processing means (not illustrated) connected to the detector 740.

For a diagnostic system, the radiation source 735 is a diagnostic radiation source providing diagnostic (most often low energy, i.e. in the order of keV) radiation. The detector 740 is then adapted to capture radiation passing through a patient lying on the couch. The image processing means then provides anatomical information, most often an image, of the irradiated portion of the patient. Different imaging techniques and therefore different diagnostic machines may be used, as has been briefly discussed above.

In a radiation therapy system, the radiation source 735 irradiates a target volume in the patient with a high energy (in the order of MeV) radiation beam. The detector 740 may be adapted for providing a portal image of the target volume based on the detected radiation. In addition, the radiation therapy machine may be provided with a diagnostic imaging system, including a diagnostic radiation source and associated detector. The diagnostic radiation source and detector can then be arranged on the gantry, substantially perpendicular to the radiation therapy source 735 and the portal imaging detector 740. However, the diagnostic radiation source is preferably arranged in the radiation head 730 together with the therapy radiation source 735 or on the outside of the radiation head 735.

Instead of using two detectors, one portal image detector adapted for the high-energy therapy radiation and one detector associated with the low-energy diagnostic radiation, one single detector can be used for imaging both with the treatment radiation and with the diagnostic radiation. Such a detector is for example suggested by Brahme, et al., in WO 01/59478 A1. The detector 740 is then preferably movable along the inner circumference of the gantry 720. Thus, the detector 740 can be moved along the gantry 720 between a first position situated opposite to the radiation therapy source 735 and a second position situated opposite to the diagnostic radiation source. This means that for portal imaging, the therapy radiation will incidence on the detector, whereas for diagnostic imaging the detector 740 is moved slightly so the diagnostic radiation hits the detector 740. Typical diagnostic imaging technique used in the radiation machine is CT-imaging. As a complement, or instead of the CT system, PET imaging can be employed in the radiation machine. In such a case, at least two dedicated detectors are circumferentially arranged in the gantry, on opposite sides of the rotation axis of the gantry. These PET detectors are preferably situated in a respective hallow in the gantry when not used. Before use, they are moved out from the hollows in an axial movement along the gantry rotation axis until the target in the patient to be diagnosed is situated between the two detectors. The information obtained from the PET system can be used as a complement to portal imaging, and/or other diagnostic imaging data, giving functional information of the patient by detecting distribution and activity of radioactive material introduced into the patient.

The first couch unit 1 of the body-supporting couch is arranged on one side of the radiation machine 700 so that the first table top portion 10 may be moved in through the gantry 720. In addition, the rotation axis 750 of the first couch unit 1 (the rotating disk 35) preferably coincidences with the radiation beam when the radiation source 735 is in its uppermost position, as in FIG. 8.

The second couch unit 2 is then arranged on the other opposite side of the radiation machine 700 with the second table top portion 20 extending towards the first couch unit 1. The second couch unit 2 may be arranged on the floor next to the radiation machine 700, on a nearby wall or preferably, as in FIGS. 7 and 8, on the gantry support 710 of the radiation machine 700.

Alternatively, the placement of the first 1 and second 2 couch unit relative the radiation machine 700 may be interchanged. In such a case, the second couch unit 2 is placed facing the gantry 720, whereas the first couch unit 1 is arranged on the opposite side of the radiation machine 700. As a result, a patient on the couch is lying with his/her head "in front of" the gantry 720 and the legs and feet "behind" the gantry support 710, when going along the rotation axis 760 of the machine 700 from the gantry support 710 ("back side") to the gantry 720 ("front side").

In order to facilitate lying down, a slidable material, may cover a part of the first table top portion 10. When the patient is lying on the first table top portion 10 he/she is pushed on the slidable material until his/her head is close to the other side (the side with the first docking means 15) of the first table top portion 10.

Figure 9A:
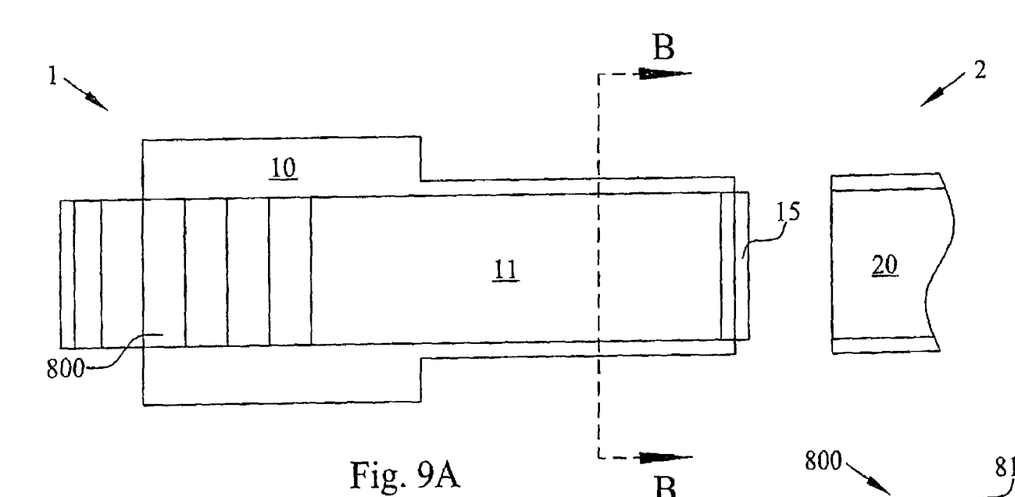
FIG. 9A is a top view of a body-supporting couch according to the present invention including elements allowing an easy getting onto the couch.
Figure 9B:
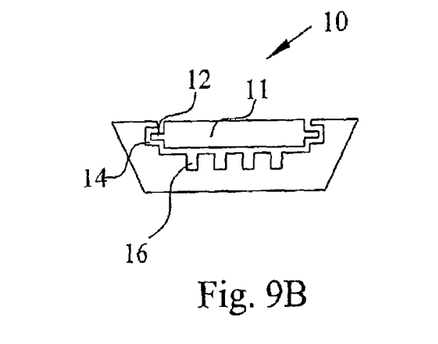
FIG. 9B is a sectional view of the couch illustrated in FIG. 9A taken along the line B—B.

FIG. 9A illustrates a top view of a body-supporting couch according to the present invention including elements allowing an easy getting onto/off the couch. In this embodiment a sheet 11 can be moved relative the first table top portion 10 of the first couch unit 1. This sheet 11 runs in slots arranged in the first table top portion 10, which is more clearly seen in the sectional view in FIG. 9B of the couch in FIG. 9A taken along the line B—B. In FIG. 9B, protrusions 12 extending from the movable sheet 11 runs in dedicated slots 13 in the first table top portion 10. In order to facilitate movement of the sheet 11 relative the table portion 10, compressed air may be provided from air outlets 16 in the first table top portion 10. In such a case, the compressed air reduces any friction between the movable sheet 11 and the table top 10. Also other solutions for facilitating movement of the sheet 11 can be used in the body-supporting couch. Similar slots are also provided in the second couch unit 20. Thus, the sheet 11 can be moved into the second couch unit 2 covering partly both the first table top portion 10 and the second table top portion 20. The movable sheet 11 is preferably made of a strong and inflexible material with low radiation absorption, such as honeycomb carbon fiber discussed above.

The sheet 11 is moved by driving elements provided in the first couch unit 1. For example, two driving shafts or wheels with a chain running therebetween can be arranged in the first table top portion 10. Underneath the sheet 11, a hold is arranged for connecting the sheet 11 to the chain. Thus, when the driving shafts, gears or wheels are rotated the chain pulls the sheet 11 to allow a longitudinal movement of the sheet 11 relative the first table top portion 10. In order to reduce radiation absorption, the driving elements and hold are preferably arranged away from the portion of the first couch unit where the actual radiation incidence on a patient lying on the couch.

The length of the sheet 11 is preferably large enough to allow a patient to lie thereon, i.e. the sheet 11 should at least cover the length from the seat or bottom of the patient to his/her head. The legs of the patient are then placed on a belt-formed wire 800, which is movable relative the first couch unit.

Figure 9C:
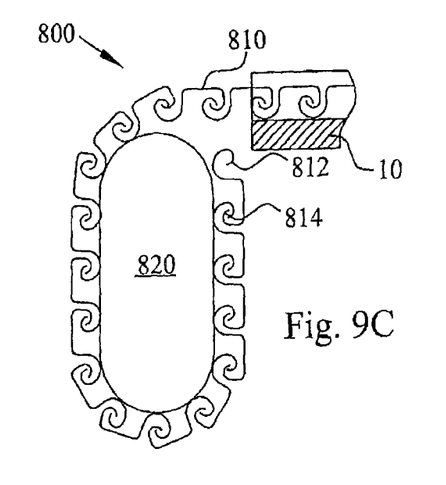
FIG. 9C illustrates a wire system used in the couch of FIG. 9A.

A wire system usable with the invention is illustrated in FIG. 9C. The wire 800 could be composed of several interconnected links 810 having an arc-shaped first side 812 and a gripping second side 814. The gripping side 814 of a first link 810 grips and engages with the arc-shaped side of a second link, thereby interconnecting them. This second link is in turn connected to a third link through its gripping side and the arc-shaped side of the third link. The wire 800 is stored in a wire magazine 820 arranged in or in the connection of the first couch unit. The wire 800 then runs from the magazine 820 into the first couch unit, for example into the first table top portion 10 below the movable sheet, discussed above. The links 810 of the wire 800 can be made of metal, plastic or any other hardwearing material.

With reference to FIGS. 7 and 9A–C, when a patient is to be positioned on the couch, the first table top portion 10 is first moved out from the second couch unit 2 and the gantry 720 and is lowered. It may also be advantageous to rotate the first couch unit 1 before getting thereon depending the relative position of other appliances, apparatuses and obstacles in the room. The movable sheet 11 is moved towards the end of the first table top portion 10 that is facing away from the radiation machine 700. Now the body-supporting couch according to the invention is in a position allowing an easy getting on by a patient. Firstly, the patient sits down on the sheet 11, e.g. from one of the sides of the first couch unit 1. Medical personnel then turns the patient and places his/her feet on the wire 800, arranged in the end of the first couch unit 1. Now the patient lies down on the movable sheet 11 lying with his/her bottom close to one end of the sheet 11 and his/her head in the vicinity of the other opposite end.

A laser system for aligning and positioning the patient on the couch, e.g. according to a dose or treatment plan, is preferably arranged in the room. A typical alignment and positioning system may be a system using the isocentric method known to the art. This system is then adapted for positioning the patient when the first table top portion 10 and the patient is lowered. This means that a correct position of the patient at this low height corresponds to the intended patient position when the first table top 10 is raised, moved in through the gantry 720 and connected to the second table top portion 20. The low height facilitates and makes any manual repositioning of the patient by medical personnel comfortable.

Thereafter, the first table top portion 10 is raised and moved into the gantry 720. The first docking means 15 then engages and docks with the second docking means 25, possible also locks thereto. The sheet 11 is now moved towards the second couch unit 2 in the dedicated slots 13 by the driving elements. At the same time as the sheet 11 and the patient thereon are moved, the patient's feet are lying on the wire 800, which passively are moved together with the sheet 11 and patient. Thus, the wire 800 is unrolled from the magazine 820 and slides into the first couch unit 1. The sheet 11 continues movement until the patient is situated to allow radiation beams from the radiation source to irradiate the target volume. In this position, the sheet 11 most often is moved partly into the second couch unit 2 covering both a part of the first 10 and second 20 table top portion.

If the positioning of the patient has been performed correctly, the rotation axis 760 of the gantry 720 and the rotation axis 750 of the first couch unit 1 should preferably pass through the target volume in the patient. A second laser system may be arranged in connection to the radiation machine to check and verify the patient's position when tying ready for diagnosing or treatment.

As was mentioned above, since the rotation axis 750 of the first 1 and second 2 couch unit coincidences with the radiation beam when the radiation source 735 is in its uppermost position, it is possible to irradiate the target volume in a plan other than the orthogonal plan. Then, the first couch unit 1 is rotated through the rotating disk 35. At the same time, the second table top portion 20 is moved along the arc portion so that the table top and patient is positioned with a non-zero angle relative the rotation axis 760 of the gantry 720.

Figure 10:
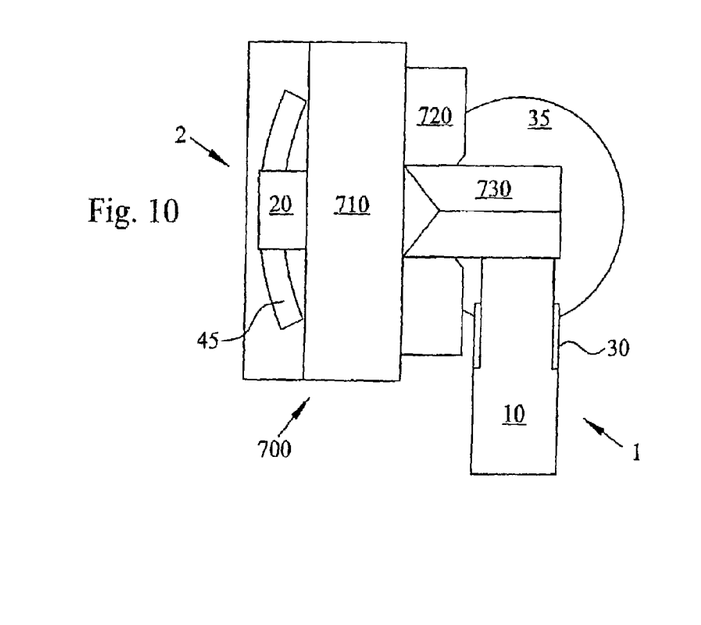
FIG. 10 is a top view of the system illustrated in FIG. 8 with the body-supporting couch in a position adapted for radiation of a patient's head.

The body-supporting couch according to the present invention is also adapted for irradiating the head of a patient. FIG. 10 is a top view of a radiation system delivering radiation to the patient's head. For such a radiation, once the patient is positioned on the first table top portion 10, it is raised and turned 90', i.e. perpendicular to the rotation axis of the gantry 720. The couch is very stable also in this position although the first table top portion 10 is not connection to the second table top portion 20. This is because the first table top portion 10 and the patient is not moved and extended so far from the first table top support 30. Thus, the patient's center of gravity is close to or above the first table top support 30. Therefore, any bending of the first table top portion 10 caused by the weight of the patient is very small even with only one table support.

For the radiation therapy or diagnosing discussed in connection with FIG. 10, i.e. the first table top portion is positioned perpendicular to the rotation axis of the gantry, the docking means of the first couch unit is preferably covered by a protective cover or case. This cover protects the first docking means from any mechanical wearing or from hitting any appliance in the room when turning the first table top portion. A removable metal or plastic case, arranged covering the first docking means, can be used for this purpose. The case or cover is then removed for conventional use, when the first table top portion is to be connected to the second table top portion by the docking means. A similar cover can also be used for the corresponding second docking means of the second couch unit.

The embodiments described above are merely given as examples, and it should be understood that the present invention is not limited thereto. Further modifications, changes and improvements that retain the basic underlying principles disclosed and claimed herein are within the scope and spirit of the invention.

The invention claimed is:

1. A body-supporting couch comprising:
a first couch unit in turn comprising:
a first table top support comprising an upper and a lower first table top support, respectively, said upper first table top support is rotatably arranged on the lower first table top support for rotation around a rotation axis;
a first elongated table top portion supported by the first table top support and extending substantially horizontally from the first table top support, said first table top portion having a first docking means arranged in an end thereof and being adapted for carrying a patient positioned on the first table top portion; and
means, arranged in the first couch unit and connected to the first elongated table top portion and to the first table top support, for moving the first table top portion relative the first table top support along a longitudinal axis of the first table top portion; and
a second couch unit in turn comprising:
a second table top support comprising a circle arc portion, the center of curvature of which is situated at the rotation axis of the first couch unit;
a second table top portion supported by the second table top support and having a second docking means arranged in an end thereof facing the first couch unit, said second docking means is engagable upon contact with the first docking means; and
means for moving the second table top portion along the circle arc portion.

2. The body-supporting couch according to claim 1, wherein the first couch unit comprises height-adjusting means for moving the first table top portion along a substantially vertical axis.

3. The body-supporting couch according to claim 1, wherein the second couch unit further comprises:
means for moving the second table top portion relative the second table top support along a horizontal axis parallel with the longitudinal axis of the first table top portion when the first docking means is engaged with the second docking means; and
biasing means connected to the second table top portion, for providing a biasing on the second table top portion along the horizontal axis towards the first couch unit.

4. The body-supporting couch according to claim 1, wherein the first couch unit comprises means for moving the first table top portion relative the first table top support along a horizontal axis substantially perpendicular to the longitudinal axis of the first table top portion.

5. The body-supporting couch according to claim 4, wherein the second couch unit comprises means for moving the second table top portion relative the second table top support along a horizontal axis substantially perpendicular to the longitudinal axis of the first table top portion when the first docking means is engaged with the second docking means.

6. The body-supporting couch according to claim 1, wherein the first and second docking means comprises locking means for locking the first table top portion to the second table top portion.

7. The body-supporting couch according to claim 1, wherein the second docking means comprises a guiding member for guiding the first docking means and the first table top portion into correct position relative the second table top portion, whereby said first and said second table top portion form a continuous table top.

8. The body-supporting couch according to claim 1, wherein the first table top portion and second table top portion comprise a slot system and the first couch unit comprises a movable sheet and driving means for moving the sheet relative the first couch unit in the slot system.

9. A radiation system comprising a radiation machine and a body-supporting couch,
said radiation machine comprises:
a gantry support unit with a cylindrical opening therethrough;
a ring-shaped gantry rotatably supported by the gantry support unit, the rotation axis of the gantry is aligned with the axis of the opening, and
a radiation head including a radiation source circumferentially arranged on the gantry,
said body-supporting couch comprises:

a first couch support unit arranged on a first side of the gantry, said first couch support unit in turn comprises:
  a first table top support comprising an upper and a lower first table top support, respectively, said upper first table top support is rotatably arranged on the lower first table top support for rotation around a rotation axis;
  a first elongated table top portion supported by the first table top support and extendable substantially horizontally from the first table top support through at least a portion of the gantry, said first table top portion having a first docking means arranged in an end thereof and being adapted for carrying a patient positioned on the first table top portion; and
  means, arranged in the first couch unit and connected to the first elongated table top portion and to the first table top support, for moving the first table top portion relative the first table top support along a longitudinal axis of the first table top portion; and
a second couch unit arranged on a second opposite side of the gantry, said second couch unit in turn comprises:
  a second table top support comprising a circle arc portion, the center of curvature of which is situated at the rotation axis of the first couch unit;
  a second table top portion supported by the second table top support and having a second docking means arranged in an end thereof facing the first couch unit, said second docking means is engagable upon contact with the first docking means; and
  means for moving the second table top portion along the circle arc portion.

10. The system according to claim 9, wherein the second couch unit is mounted on the gantry support unit.

11. The system according to claim 9, wherein the first couch support unit comprises height-adjusting means for moving the first table top portion along a substantially vertical axis.

12. The system according to claim 9, wherein the second couch unit further comprises:
  means for moving the second table top portion relative the second table top support along a horizontal axis parallel with the longitudinal axis of the first table top portion when the first docking means is engaged with the second docking means; and
  biasing means connected to the second table top portion, for providing a biasing on the second table top portion along the horizontal axis towards the first couch unit.

13. The system according to claim 9, wherein the system is a radiation therapy system and the radiation source is adapted for delivering therapy radiation to a patient on the body-supporting couch, said system further including a diagnostic imaging system, in turn comprising:
  a diagnostic radiation source supported by the gantry to direct diagnostic radiation onto the object;
  a detector unit, arranged on the gantry, responsive to diagnostic radiation passing through the patient and outputting a signal representative of the detected radiation; and
  a processing means connected to the detector unit, for providing an image of the object based on the received output signal from the detector unit.

* * * * *